United States Patent [19]

Abe et al.

[11] Patent Number: 5,376,620

[45] Date of Patent: Dec. 27, 1994

[54] SULFONAMIDE DERIVATIVE, PROCESS FOR PREPARING THE SAME AND HERBICIDE USING THE SAME

[75] Inventors: Takaaki Abe; Yuji Akiyoshi; Hiroshi Shiraishi; Ikuo Shiraishi; Mikio Kojima; Takashi Hayama; Takaaki Kuwata, all of Ube, Japan

[73] Assignee: Ube Industries, Ltd., Yamaguchi, Japan

[21] Appl. No.: 41,998

[22] Filed: Apr. 2, 1993

[30] Foreign Application Priority Data

| Apr. 17, 1992 | [JP] | Japan | 4-140865 |
| Apr. 24, 1992 | [JP] | Japan | 4-149795 |
| Jun. 26, 1992 | [JP] | Japan | 4-208377 |
| Jun. 30, 1992 | [JP] | Japan | 4-210603 |
| Mar. 12, 1993 | [JP] | Japan | 5-052292 |

[51] Int. Cl.$^5$ .................. C07D 239/60; A01N 43/54
[52] U.S. Cl. .................. 504/243; 544/123; 544/300; 544/301; 504/225
[58] Field of Search ............ 504/243, 225; 544/300, 544/301, 123

[56] References Cited

FOREIGN PATENT DOCUMENTS

| 0411706 | 2/1991 | European Pat. Off. . |
| 0517215 | 12/1992 | European Pat. Off. . |
| 3-193765 | 8/1991 | Japan . |
| 200722 | 9/1991 | Japan . |
| 3-200772 | 9/1991 | Japan . |
| 279210 | 10/1993 | Japan . |

*Primary Examiner*—John M. Ford

*Attorney, Agent, or Firm*—Finnegan, Henderson, Farabow, Garrett & Dunner

[57] ABSTRACT

Disclosed are a sulfonamide compound represented by the following formula (I):

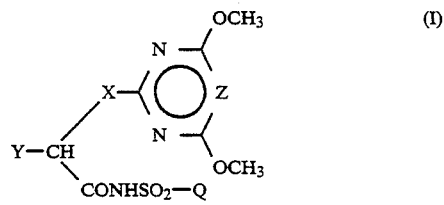

wherein Y represents a lower akyl group, a lower alkenyl group, a lower alkynyl group, a halo-lower alkyl group, a cyano-lower alkyl group or —C(CH$_3$)$_2$(OR$^1$) where R$^1$ represents a lower akyl group, a lower alkenyl group, a lower alkynyl group, a halo-lower alkyl group or a cyano-lower alkyl group; Q represents a substituted or unsubstituted pyridyl group or —NR$^2$R$^3$ where R$^2$ represents a hydrogen atom, a lower alkyl group, a lower alkoxy group; and R$^3$ represents a lower alkyl group, a lower alkenyl group, a lower alkynyl group, a phenyl group or a benzyl group; or R$^2$ and R$^3$ may be combined to form a cycloamino group; X represents an oxygen atom or a sulfur atom; and Z represents a nitrogen atom or —CH= group;

processes for preparing the same and a herbicide containing the same as an active ingredient(s).

9 Claims, No Drawings

SULFONAMIDE DERIVATIVE, PROCESS FOR PREPARING THE SAME AND HERBICIDE USING THE SAME

BACKGROUND OF THE INVENTION

This invention relates to a novel sulfonamide derivative, process for preparing the same and a herbicide containing the same as an active ingredient.

Many herbicides have heretofore been developed for promoting labor-saving of farm practices and increase in productivity of crops. Conventional herbicides are, however, not sufficient in herbicidal effect, e.g. insufficient in selective herbicidal effect to crops such as cotton and soy bean, and also not sufficiently satisfactory in the point of safety to creatures. Thus, in order to solve these problems, development of a novel herbicide has been demanded.

Sulfonamide derivatives of the present invention are novel compounds and their herbicidal effect have not yet been known.

As a compound similar to the sulfonamide derivative of the present invention, there has been known, for example, compounds disclosed in Japanese Provisional Patent Publication No. 85262/1990, EP-A-0 347 811, EP-A-0 411 706 and EP-A-0 517 215, and it has been also known that these compounds have herbicidal activities. However, herbicidal effects of these compounds are insufficient, and thus, it has been desired to develop a novel herbicide having more excellent activities.

SUMMARY OF THE INVENTION

An object of the present invention is to provide a novel sulfonamide derivative, a process for preparing the same and a herbicide containing said compound as an active ingredient.

The present inventors have studied intensively in order to solve the above problems, and consequently found that a novel sulfonamide derivative shows more excellent herbicidal effect against annual rice plant weeds and annual broad-leaved weeds and shows selectivity to crops such as cotton, and also found a process for preparing the same with high yields, to accomplish the present invention.

The present invention is described below.

That is, the first invention is concerned to a sulfonamide derivative represented by the following formula (I):

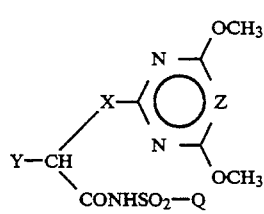

wherein Y represents a lower akyl group or —C(CH$_3$)$_2$(OR$^1$) where R$^1$ represents a lower akyl group, a lower alkenyl group, a lower alkynyl group, a halo-lower alkyl group or a cyano-lower alkyl group; Q represents a substituted or unsubstituted pyridyl group or —NR$^2$R$^3$ where R$^2$ represents a hydrogen atom, a lower alkyl group or a lower alkoxy group; and R$^3$ represents a lower alkyl group, a lower alkenyl group, a lower alkynyl group, a phenyl group or a benzyl group; or R$^2$ and R$^3$ may be combined to form a cycloamino group;

X represents an oxygen atom or a sulfur atom; and

Z represents a nitrogen atom or —CH= group.

The second invention is concerned to a 3-alkoxy-N-(N-substituted amino)sulfonylalkanoic acid derivative represented by the following formula (Ia):

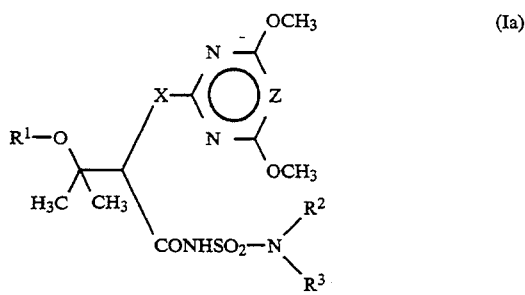

wherein R$^1$, R$^2$, R$^3$, X and Z each have the same meanings as defined above.

The third invention is concerned to an alkylaminosulfonamide derivative represented by the following formula (Ib):

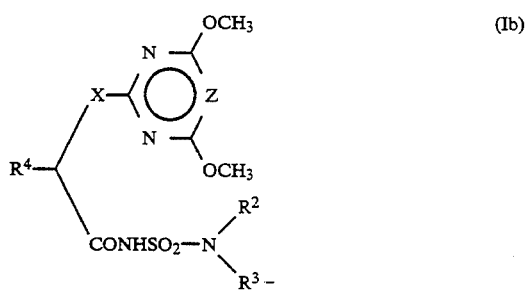

wherein R$^2$, R$^3$, X and Z each have the same meanings as defined above, and R$^4$ represents a lower alkyl group.

The fourth invention is concerned to a 3-alkoxy-N-pyridylsulfonylalkanoic acid amide derivative represented by the following formula (Ic):

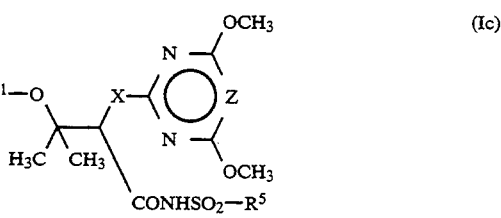

wherein R$^1$, X and Z each have the same meanings as defined above; and R$^5$ represents a substituted or unsubstituted pyridyl group.

The fifth invention is concerned to a 2-pyrimidinyl-thioalkanoic acid derivative represented by the following formula (Id):

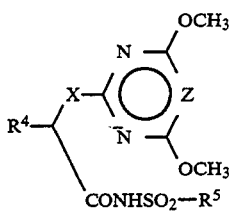

wherein R⁴ represents a lower alkyl group; R⁵ represents a substituted or unsubstituted pyridyl group; and X and Z each have the same meanings as defined above.

The sixth invention is concerned to a process for preparing the sulfonamide derivative represented by the above formula (I), which comprises reacting a compound represented by the following formula (II):

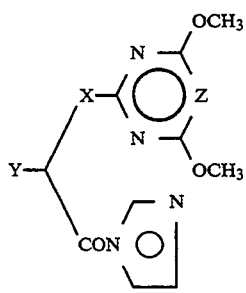

wherein Y, X and Z each have the same meanings as defined above,
with a compound represented by the following formula (III):

MHNSO₂—Q     (III)

wherein M represents an alkali metal and Q has the same meaning as defined above.

The seventh invention is concerned to a process for preparing the sulfonamide derivative represented by the above formula (I), which comprises reacting a compound represented by the following formula (IV):

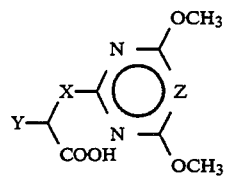

wherein Y, X and Z each have the same meanings as defined above, provided that the case where Y is —C(CH₃)₂(OR¹), X is a sulfur atom is excluded, with a compound represented by the following formula (V):

H₂NSO₂—Q     (V)

wherein Q has the same meaning as defined above.

The eighth invention is concerned to a herbicide comprising the sulfonamide derivative represented by the above formula (I) as an active ingredient.

DESCRIPTION OF THE PREFERRED EMBODIMENTS

In the following, the present invention is explained in detail.

In the novel sulfonamide derivative (I) including the compounds of the formulae (Ia) to (Id) which are the desired compounds of the present invention and the compounds (II) to (V) which are starting materials thereof, $R^1$, $R^2$, $R^3$, $R^4$, $R^5$, M, Q, X, Y and Z are as described below.

Y represents a lower alkyl group (which corresponds to $R^4$) or —C(CH₃)₂(OR¹) where $R^1$ represents a lower alkyl group, a lower alkenyl group, a lower alkynyl group, a halo-lower alkyl group or a cyano-lower alkyl group; and the alkyl group may be a straight or branched alkyl group having 1 to 6 carbon atoms, preferably 1 to 4, more preferably 2 to 4 (e.g. an ethyl group, an n-propyl group, an i-propyl group and a t-butyl group). As the lower alkyl group for $R^1$, there may be mentioned a straight or branched one having 1 to 6 carbon atoms, preferably 1 to 4, more preferably 1 to 3 (e.g. a methyl group, an ethyl group, an n-propyl group and an i-propyl group). The lower alkenyl group for $R^1$ may include a straight or branched one having 2 to 6 carbon atoms, preferably 2 to 3, more preferably a propenyl group (e.g. an allyl group). The lower alkynyl group for $R^1$ may include a straight or branched one having 2 to 6 carbon atoms, preferably 2 to 3, more preferably a propynyl group (e.g. a propargyl group). The halo-lower alkyl group may include a straight or branched one having 1 to 6 carbon atoms (as the halogen atom, there may be mentioned a fluorine atom, a chlorine atom, a bromine atom and an iodine atom), preferably 1 to 4, more preferably 1 to 2; and preferred halogen atom may include a fluorine atom and a chlorine atom. Most preferred halo-lower alkyl group includes, for example, a fluoroethyl group and a chloroethyl group. The cyano-lower alkyl group may include a straight or branched one having 1 to 6 carbon atoms, preferably 1 to 3 (e.g. a cyanoethyl group).

Q represents a substituted or unsubstituted pyridyl group (which corresponds to $R^5$) or —NR²R³. The pyridyl group may include 2-, 3- or 4-pyridyl group. The substituted position of the substituted pyridyl group is preferably 2-, 3-, 4- and/or 5-position, and the substituent for the substituted pyridyl group may include a lower alkyl group, a halogen atom, a halo-lower alkyl group and a lower alkoxy group. The lower alkyl group may include a straight or branched one having 1 to 6 carbon atoms, preferably 1 to 4, more preferably 1 to 3 (e.g. a methyl group, an ethyl group, an n-propyl group and an i-propyl group) and preferred substitution position for the pyridyl group is 2- and/or 3-position. The halogen atom may include a fluorine atom, a chlorine atom, a bromine atom and an iodine atom, preferably a chlorine atom, and preferred substitution position for the pyridyl group is 3-position. The halo-lower alkyl group may include a straight or branched one having 1 to 6 carbon atoms (as the halogen atom, a fluorine atom, a chlorine atom, a bromine atom and an iodine atom may be mentioned), preferably 1 to 4, more preferably 1 to 2; preferred halogen atom may include a fluorine atom and a chlorine atom, and preferred substitution position for the pyridyl group is 3-, 4- and/or 5-position. Most preferred halo-lower alkyl group includes, for example, a fluoromethyl group. The lower alkoxy group may include a straight or branched one having 1 to 6 carbon atoms, preferably a methoxy group and an ethoxy group.

$R^2$ represents a hydrogen atom, a lower alkyl group or a lower alkoxy group; and the lower alkyl group may include a straight or branched one having 1 to 6 carbon atoms, preferably 1 to 3 (e.g. a methyl group) and the lower alkoxy group may include a straight or branched one having 1 to 6 carbon atoms, preferably 1 to 3 (e.g. a methoxy group).

$R^3$ represents a lower alkyl group, a lower alkenyl group, a lower alkynyl group, a phenyl group or a benzyl group; and the lower alkyl group may include a straight or branched one having 1 to 6 carbon atoms (e.g. a methyl group, an ethyl group, an n-propyl group, an i-propyl group, an n-butyl group, a t-butyl group, an n-pentyl group and an n-hexyl group), the lower alkenyl group may include a straight or branched one having 2 to 6 carbon atoms, preferably 2 to 4, more preferably a propenyl group (e.g. an allyl group), the lower alkynyl group may include a straight or branched one having 2 to 6 carbon atoms, preferably 2 to 4, more preferably a propynyl group (e.g. a propargyl group), the phenyl group may include a substituted or unsubstituted phenyl group, preferably an unsubstituted one, and the benzyl group may include a substituted or unsubstituted benzyl group, preferably an unsubstituted one.

Or else, $R^2$ and $R^3$ may be combined to form a cycloamino group having, e.g. 2 to 10 carbon atoms, preferably a cycloamino group having 2 to 7 carbon atoms, more preferably 2 to 5 carbon atoms (e.g. a piperazyl group and a morpholino group).

X represents an oxygen atom or a sulfur atom.

Z represents a nitrogen atom or —CH= group.

M in the formula (III) represents an alkali metal such as sodium and potassium.

The novel sulfonamide derivative (I) which is a desired compound may include an optical isomer based on an asymmetric carbon atom.

The compound (I) can be prepared by, for example, Preparation method 1 and Preparation method 2 shown below.

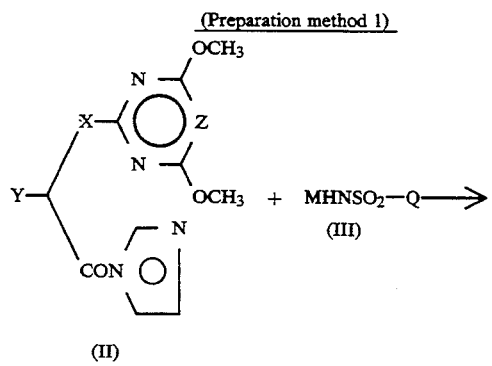

wherein Q, Y, X and Z each have the same meanings as defined above.

The compound (I) can be prepared by reacting the starting compound (II) and the starting compound (III) in a solvent.

The compound (II) can be prepared easily by, for example, reacting a corresponding carboxylic acid and a commercially available N,N-carbonyldiimidazole in a solvent such as N,N-dimethylformamide, diethyl ether, dioxane, tetrahydrofuran (THF), methylene chloride, chloroform and toluene.

As the compound (II), there may be mentioned, for example, the respective compounds (referred to as Compounds $(II)_1$ to $(II)_{116}$) comprising the respective kinds of substituted groups corresponding to Compounds No. 1 to No. 116 shown in Table 1 (for example, the compound (II) corresponding to Compound No. 2 is referred to as Compound $(II)_2$, and this Compound $(II)_2$ means a compound wherein Y is $C(CH_3)_2(OCH_3)$, X is a sulfur atom and Z is —CH= in the compound (II)).

The compound (III) may be easily prepared by reacting a sulfonamide (it can be prepared by reacting a sulfonyl chloride prepared according to the method described in Shin-Jikken Kagaku Koza (Maruzen), vol. III, p. 1806 or J. Am. Chem. Soc., vol. 82, p. 1132 (1960), and ammonia) and an alkaline aqueous solution or an alkali metal alkoxide.

As the compound (III), there may be mentioned, for example, the respective compounds (referred to as Compounds $(III)_1$ to $(III)_{116}$) comprising the respective kinds of substituted groups corresponding to Compounds No. 1 to No. 116 shown in Table 1 (for example, the compound (III) corresponding to Compound No. 2 is referred to as Compound $(III)_2$, and this Compound $(III)_2$ means a compound wherein Q is $N(CH_3)_2$ and M is an alkali metal in the compound (III)).

The solvent used for preparing the compound (I) is not particularly limited so long as it does not participate in the present reaction directly, and may include, for example, ethers such as diethyl ether, THF and 1,4-dioxane; bipolar aprotic solvents such as N,N-dimethylformamide and dimethyl sulfoxide; nitriles such as acetonitrile; and a mixture of the above solvents.

The reaction for preparing the compound (I) can be carried out at a reaction concentration of 5 to 80%.

In the preparation method, the ratio of using the starting compound (II) and (III) is that 0.5 to 2 mole, preferably 1 to 1.5 mole of the compound (III) per mole of the compound (II).

The reaction temperature is not particularly limited so long as it is a boiling point of a solvent to be used or lower, but the reaction can be carried out generally at —5° to 30° C., preferably 0° to 20° C.

The reaction time varies depending on the above concentration and temperature, but may be generally carried out for 1 to 24 hours.

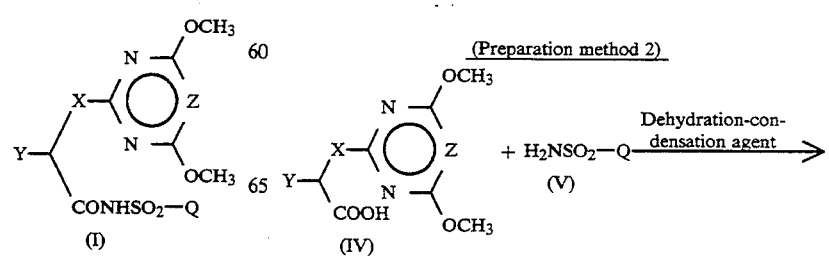

-continued
(Preparation method 2)

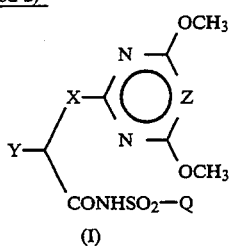

wherein Q, Y and Z each have the same meanings as defined above, provided that the case where Y is —C(CH$_3$)$_2$(OR$^1$), X is a sulfur atom is excluded.

The compound (I) can be prepared by reacting the compound (IV) and the compound (V) in a solvent in the presence of a dehydration-condensation agent.

The compound (IV) wherein Y is a lower alkyl group can be easily prepared according to the method as described in Japanese Provisional Patent Publication No. 85262/1990 and the compound of the formula (IV) wherein Y is C(CH$_3$)$_2$(OR$^1$) and X is an oxygen atom can be easily prepared by reacting a 3-alkoxy-2-hydroxyalkanoic acid eater and a pyrimidine (or a triazine) in a solvent in the presence of a base and then hydrolyzing the resulting ester as shown below.

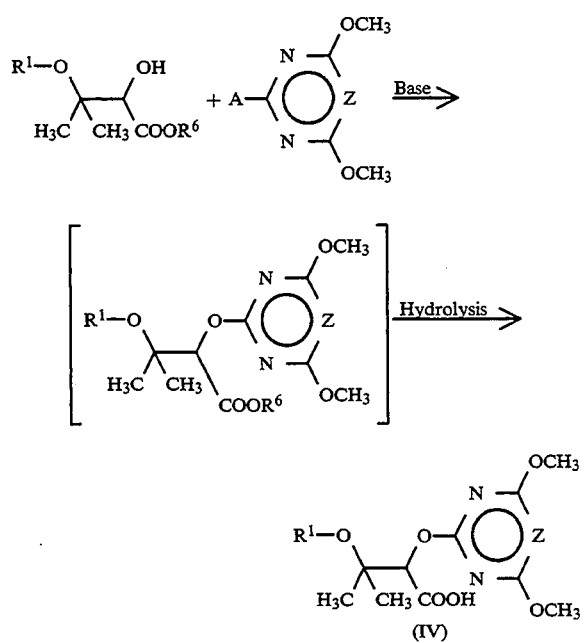

wherein R$^1$ and Z have the same meanings as defined above, R$^6$ represents a hydrogen atom, a lower alkyl group, and A represents a halogen atom or a lower alkylsulfonyl group.

As the compound (IV), there may be mentioned, for example, the respective compounds (referred to as Compounds (IV)$_1$ to (IV)$_{116}$) comprising the respective kinds of substituted groups corresponding to the compounds wherein Y represents C(CH$_3$)$_2$(OR$^1$), X is an oxygen atom shown in Table 1 and all the compounds wherein Y represents a lower alkyl group in Table 1, (for example, the compound (IV) corresponding to Compound No. 1 is referred to as Compound (IV)$_1$, and this Compound (IV)$_1$ means a compound wherein Y is C(CH$_3$)$_2$(OCH$_3$), X is an oxygen atom and Z is —CH= in the compound (IV)).

The compound (V) may be used a commercially available product or may be easily prepared by reacting the sulfonyl chloride according to the above Preparation method 1 and ammonia.

As the compound (V), there may be mentioned, for example, the respective compounds (referred to as Compounds (V)$_1$ to (V)$_{116}$) comprising the respective kinds of substituted groups corresponding to the compounds wherein Y represents C(CH$_3$)$_2$(OR$^1$), X is an oxygen atom shown in Table 1 and all the compounds wherein Y represents a lower alkyl group in Table 1, (for example, the compound (V) corresponding to Compound No. 1 is referred to as Compound (V)$_1$, and this Compound (V)$_1$ means a compound wherein Q is N(CH$_3$)$_2$ in the compound (V)).

The solvent used for preparing the compound (I) is not particularly limited so long as it does not participate in the present reaction directly, and may include, for example, substituted or unsubstituted aromatic hydrocarbons such as benzene, toluene, xylene and chlorobenzene; halogenated hydrocarbons such as chloroform and methylene chloride; bipolar aprotic solvents such as N,N-dimethylformamide and dimethyl sulfoxide; nitriles such as acetonitrile; ethers such as diethyl ether, THF and dioxane; and a mixture of the above solvents.

As the dehydration-condensation agent, there may be mentioned, for example, dicyclohexylcarbodiimide (DCC) and 1-ethyl-3-(3-dimethylaminopropyl)carbodiimide hydrochloride (available from Dojin Kagaku Kenkyusho under the trade name of WSC).

The reaction for preparing the compound (I) can be carried out at a reaction concentration of 5 to 80%.

In the preparation method, the ratio of using the starting compound (IV) and the compound (V) is that 0.5 to 2 mole, preferably 1 to 1.5 mole of the compound (V) per mole of the starting compound (IV).

The reaction temperature is not particularly limited so long as it is a boiling point of a solvent to be used or lower, but the reaction can be carried out generally at 0° to 50° C.

The reaction time varies depending on the above concentration and temperature, but may be generally carried out for 1 to 24 hours.

As the compound (I), there may be mentioned, for example, the respective compounds (referred to as Compounds 1 to 116) comprising the respective kinds of substituted groups corresponding to Compounds No. 1 to No. 116 shown in Table 1 (for example, the compound (I) corresponding to Compound No. 1 is referred to as Compound 1, and this Compound 1 means a compound wherein Y is C(CH$_3$)$_2$(OCH$_3$), Q is N(CH$_3$)$_2$, X is O and Z is —CH= in the compound (I)).

The herbicide containing the compound (I) as an active ingredient has high selectivity and also shows excellent herbicidal effect.

That is, the herbicide of the present invention shows excellent herbicidal effect on annual weeds and perennial weeds grown in paddy fields and upland fields, and its herbicidal effect is particularly remarkable in annual grass weeds (e.g. crabgrass (manna-grass), barnyardgrass and foxtail (green panicum)), annual broad-leaved weeds (e.g. morning glory, common lambsquarter (white goosefoot), livid amaranthus, velvetleaf and cocklebur) and perennial weeds (e.g. Johnson grass, bulrush and flatstage).

The herbicide of the present invention shows excellent herbicidal effect on the weeds described above, but does not give chemical damage on field crops (e.g. cotton) at a concentration for such a treatment.

The herbicide of the present invention contains the compound (I) as an active ingredient(s).

The compound (I) can be used singly, but may be preferably used by mixing with a carrier, a surfactant, a dispersant and an auxiliary (for example, prepared as a composition such as a dust, an emulsion, a fine granule, a granule, a wettable powder, an oily suspension and an aerosol) according to a conventional method.

As the carrier, there may be mentioned, for example, a solid carrier such as talc, mica, bentonite, clay, kaolin, diatomaceous earth, white carbon, vermiculite, dolomite, zeolite, slaked lime, siliceous sand, silicic anhydride, ammonium sulfate, urea, wood powder, starch and cellulose; a liquid carrier such as hydrocarbons (e.g. kerosine and mineral oil), aromatic hydrocarbons (e.g. benzene, toluene and xylene), chlorinated hydrocarbons (e.g. chloroform and carbon tetrachloride), ethers (e.g. dioxane and tetrahydrofuran), ketones (e.g. acetone, cyclohexanone and isophorone), esters (e.g. ethyl acetate, ethylene glycol acetate and dibutyl maleate), alcohols (e.g. methanol, n-hexanol and ethylene glycol), polar solvents (e.g. dimethylformamide and dimethylsulfoxide) and water; and a gas carrier such as air, nitrogen, carbonic acid gas and freon (in the case of a gas carrier, mixed spray can be carried out).

As the surfactant which can be used for improving attachment of the present herbicide to and absorption thereof in plants, and improving characteristics such as dispersion, emulsification and spreading of the herbicide, there may be mentioned nonionic, anionic, cationic or amphoteric surfactants (e.g. alcohol sulfates, alkylsulfonates, lignin sulfonates and polyoxyethylene glycol ethers). Further, for improving properties of preparation, carboxymethyl cellulose, polyethylene glycol or gum arabic can be used as an auxiliary.

In preparation of the present herbicide, in addition to the above carrier, surfactant, dispersant and auxiliary, other agricultural chemicals (a fungicide and an insecticide), a fertilizer and a soil conditioner can be used singly or in a suitable combination, respectively, depending on the respective purposes.

When the compound (I) of the present invention is made into preparations, the concentration of the active ingredient is generally 1 to 50% by weight in an emulsion, generally 0.3 to 25% by weight in a dust, generally 1 to 90% by weight in a wettable powder, generally 0.5 to 5% by weight in a granule, generally 0.5 to 5% by weight in an oily dispersion, and generally 0.1 to 5% by weight in an aerosol.

These preparations can be provided for various uses by diluting them to have a suitable concentration and spraying them to stems and/or leaves of plants, soil and paddy field surface, or by applying them directly thereto, depending on the respective purposes.

EXAMPLES

The present invention is described in detail by referring to Examples, but the scope of the present invention is not limited by these Examples.

Example 1

(1) Synthesis of
2-(4,6-dimethoxypyrimidin-2-yl)thio-N-(N,N-dimethylamino)sulfonyl-3-methoxy-3-methylbutanoic acid amide (Compound 2)

According to Preparation method 1, the compound (I) was synthesized.

In 10 ml of N,N-dimethylformamide (DMF) was suspended 1.46 g (0.01 mol) of sodium N,N-dimethylaminosulfonamide, and to the mixture was added dropwise at 0° C. a DMF (10 ml) solution having 3.52 g (0.01 mol) of 1-[2-(4,6-dimethoxypyrimidin-2-yl)thio-3-methoxy-3-methylbutyryl]imidazole dissolved therein. After the dropwise addition, the mixture was stirred at 0° C. for 2 hours and at room temperature (20° C.) for 3 hours.

To the resulting reaction mixture was added 30 ml of a saturated citric acid aqueous solution and the mixture was extracted with ethyl acetate. The ethyl acetate layer was washed with a saturated saline solution, dried over sodium sulfate and ethyl acetate was removed under reduced pressure. The obtained residue was separated by column chromatography (Ms gel D-150-60A, available from Dokai Kagaku Kogyo, K.K., Japan, eluted by n-hexane:ethyl acetate:methanol=1:1:0.05, volume ratio, hereinafter the same) to obtain 2.85 g (yield: 70%) of the title compound as white crystal.

(2) Synthesis of
2-(4,6-dimethoxypyrimidin-2-yl)oxy-N-(N,N-dimethylamino)sulfonyl-3-methoxy-3-methylbutanoic acid amide (Compound 1)

According to Preparation method 2, the compound (I) was synthesized.

To 20 ml of methylene chloride were added 1.46 g (0.01 mol) of N,N-dimethylaminosulfonamide and 2.86 g (0.01 mol) of 2-(4,6-dimethoxypyrimidin-2-yl)oxy-3-methoxy-3-methylbutanoic acid. Further, 1.91 g (0.01 mol) of 1-ethyl-3-(3-dimethylaminopropyl)carbodiimide hydrochloride (WSC, trade name, available from Dojin Kagaku Kenkyusho, Japan) was added to the mixture and the mixture was stirred at room temperature (20° C.) for 2 hours.

After washing the reaction mixture with water, the mixture was dried over sodium sulfate and methylene chloride was removed under reduced pressure. The obtained residue was separated by column chromatography (Wako gel C-200, available from Wako Junyaku, K.K., Japan, eluted by toluene:ethyl acetate=9:1) to obtain 2.94 g (yield: 75%) of the title compound as a white oily product.

(3) Synthesis of
2-(4,6-dimethoxypyrimidin-2-yl)thio-3,3-dimethyl-N-(N,N-dimethylamino)sulfonylbutanoic acid amide (Compound 71)

According to Preparation method 1, the compound (I) was synthesized.

In 10 ml of DMF was suspended 1.46 g (0.01 mol) of sodium N,N-dimethylaminosulfonamide, and to the mixture was added dropwise at 0° C. a DMF (10 ml) solution having 3.36 g (0.01 mol) of 1-[2-(4,6-dimethoxypyrimidin-2-yl)thio-3,3-dimethylbutyryl]imidazole dissolved therein. After the dropwise addition, the mixture was stirred at 0° C. for 2 hours and at room temperature (20° C.) for 3 hours.

To the resulting reaction mixture was added 30 ml of a saturated citric acid aqueous solution and the mixture was extracted with ethyl acetate. The ethyl acetate layer was washed with a saturated saline solution, dried over sodium sulfate and ethyl acetate was removed under reduced pressure. The obtained residue was separated by column chromatography (Ms gel D-150-60A, available from Dokai Kagaku Kogyo, K. K., Japan, eluted by n-hexane:ethyl acetate:methanol=1:1:0.05) to obtain 2.94 g (yield: 75%) of the title compound as white crystal.

(4) Synthesis of 2-(4,6-dimethoxypyrimidin-2-yl)thio-N-(N,N-dimethylamino)sulfonyl-3-methoxybutanoic acid amide (Compound 68)

According to Preparation method 2, the compound (I) was synthesized.

To 20 ml of methylene chloride were added 1.46 g (0.01 mol) of N,N-dimethylaminosulfonamide and 2.72 g (0.01 mol) of 2-(4,6-dimethoxypyrimidin-2-yl)thio-3-methylbutanoic acid. Further, 1.91 g (0.01 mol) of 1-ethyl-3-(3-dimethylaminopropyl)carbodiimide hydrochloride (WSC, trade name, available from Dojin Kagaku Kenkyusho, Japan) was added to the mixture and the mixture was stirred at room temperature (20° C.) for 2 hours.

After washing the reaction mixture with water, the mixture was dried over sodium sulfate and methylene chloride was removed under reduced pressure. The obtained residue was separated by column chromatography (Wako gel C-200, available from Wako Junyaku, K. K., Japan, eluted by toluene:ethyl acetate=9:1) to obtain 3.0 g (yield: 80%) of the title compound as a colorless oily product.

(5) Synthesis of 2-(4,6-dimethoxypyrimidin-2-yl)thio-3-methoxy-3-methyl-N-(pyridin-2-yl)sulfonylbutanoic acid amide (Compound 75)

According to Preparation method 1, the compound (I) was synthesized.

In 10 ml of DMF was suspended 1.80 g (0.01 mol) of sodium 2-aminosulfonylpyridine, and to the mixture was added dropwise at 0° C. a DMF (10 ml) solution having 3.52 g (0.01 mol) of 1-[2-(4,6-dimethoxypyrimidin-2-yl)thio-3-methoxy-3-methylbutyryl]imidazole dissolved therein. After the dropwise addition, the mixture was stirred at 0° C. for 2 hours and at room temperature (20° C.) for 3 hours.

To the resulting reaction mixture was added 30 ml of a saturated citric acid aqueous solution and the mixture was extracted with ethyl acetate. The ethyl acetate layer was washed with a saturated saline solution, dried over sodium sulfate and ethyl acetate was removed under reduced pressure. The obtained residue was separated by column chromatography (Ms gel D-150-60A, available from Dokai Kagaku Kogyo, K. K., Japan, eluted by n-hexane:ethyl acetate:methanol=1:1:0.05) to obtain 3.14 g (yield: 70%) of the title compound as white crystal.

(6) Synthesis of 2-(4,6-dimethoxypyrimidin-2-yl)oxy-3-methoxy-3-methyl-N-(pyridin-2-yl)sulfonylbutanoic acid amide (Compound 74)

According to Preparation method 2, the compound (I) was synthesized.

To 20 ml of methylene chloride were added 1.57 g (0.01 mol) of 2-aminosulfonylpyridine and 2.86 g (0.01 mol) of 2-(4,6-dimethoxypyrimidin-2-yl)oxy-3-methoxy-3-methylbutanoic acid. Further, 1.91 g (0.01 mol) of 1-ethyl-3-(3-dimethylaminopropyl)carbodiimide hydrochloride (WSC, trade name, available from Dojin Kagaku Kenkyusho, Japan) was added to the mixture and the mixture was stirred at room temperature (20° C.) for 2 hours.

After washing the reaction mixture with water, the mixture was dried over sodium sulfate and methylene chloride was removed under reduced pressure. The obtained residue was separated by column chromatography (Wako gel C-200, available from Wako Junyaku, K. K., Japan, eluted by toluene:ethyl acetate=4:1) to obtain 3.24 g (yield: 75%) of the title compound as white crystal.

(7) Synthesis of 2-(4,6-dimethoxypyrimidin-2-yl)thio-3,3-dimethyl-N-(pyridin-2-yl)sulfonylbutanoic acid amide (Compound 113)

According to Preparation method 1, the compound (I) was synthesized.

In 10 ml of DMF was suspended 1.80 g (0.01 mol) of sodium 2-aminosulfonylpyridine, and to the mixture was added dropwise at 0° C. a DMF (10 ml) solution having 3.36 g (0.01 mol) of 1-[2-(4,6-dimethoxypyrimidin-2-yl)thio-3,3-dimethylbutyryl]imidazole dissolved therein. After the dropwise addition, the mixture was stirred at 0° C. for 2 hours and at 20° C. for 3 hours.

To the resulting reaction mixture was added 30 ml of a saturated citric acid aqueous solution and the mixture was extracted with ethyl acetate. The ethyl acetate layer was washed with a saturated saline solution, dried over sodium sulfate and ethyl acetate was removed under reduced pressure. The obtained residue was separated by column chromatography (Wako gel C-200, available from Wako Junyaku, K.K., Japan, eluted by toluene:ethyl acetate=4:1) to obtain 2.98 g (yield: 70%) of the title compound as white crystal.

(8) Synthesis of 2-(4,6-dimethoxypyrimidin-2-yl)thio-N-(pyridin-2-yl)sulfonyl-3-methylbutanoic acid amide (Compound 108)

According to Preparation method 2, the compound (I) was synthesized.

To 10 ml of methylene chloride were added 1.58 g (0.01 mol) of 2-aminosulfonylpyridine and 2.72 g (0.01 mol) of 2-(4,6-dimethoxypyrimidin-2-yl)thio-3-methylbutanoic acid. Further, 1.91 g (0.01 mol) of 1-ethyl-3-(3-dimethylaminopropyl)carbodiimide hydrochloride (WSC, trade name, available from Dojin Kagaku Kenkyusho, Japan) was added to the mixture and the mixture was stirred at 20° C. for 2 hours.

After washing the reaction mixture with water, the mixture was dried over sodium sulfate and methylene chloride was removed under reduced pressure. The obtained residue was separated by column chromatography (Wako gel C-200, available from Wako Junyaku, K. K., Japan, eluted by toluene:ethyl acetate=9:1) to obtain 3.3 g (yield:80%) of the title compound as a colorless oily product.

(9) Syntheses of other compounds (I) in Table 1

In the same manner as in either of the synthetic methods (1) to (8), the title compounds (I) as shown in Table 1 were obtained.

TABLE 1

$$\text{R}^1-\text{O}-\underset{\underset{\text{CH}_3}{\text{H}_3\text{C}}}{\overset{}{\text{C}}}-\underset{\text{CONHSO}_2-\text{N}\underset{\text{R}^3}{\overset{\text{R}^2}{\diagup}}}{\overset{}{\text{CH}}}-\text{X}-\underset{\text{N}}{\overset{\text{N}}{\bigcirc}}\overset{\text{OCH}_3}{\underset{\text{OCH}_3}{\diagdown}} \quad \text{(Ia)}$$

| Compound | R$^1$ | $-\text{N}\diagdown^{R^2}_{R^3}$ | X | Z | Physical property |
|---|---|---|---|---|---|
| 1 | CH$_3$ | $-\text{N}(\text{CH}_3)_2$ | O | CH | n$_D^{26.4}$ 1.4981 |
| 2 | " | " | S | " | m.p. 158~159° C. |
| 3 | " | " | " | N | m.p. 105~107° C. |
| 4 | " | piperidinyl | O | CH | m.p. 101~104° C. |
| 5 | " | " | S | " | m.p. 114~115° C. |
| 6 | " | " | " | N | Oily product |
| 7 | C$_2$H$_5$ | $-\text{N}(\text{CH}_3)_2$ | O | CH | Oily product |
| 8 | C$_2$H$_5$ | $-\text{N}(\text{CH}_3)_2$ | S | CH | |
| 9 | " | " | " | N | |
| 10 | " | piperidinyl | O | CH | n$_D^{23.8}$ 1.5084 |
| 11 | " | " | S | " | |
| 12 | " | " | " | N | |
| 13 | C$_3$H$_7$-n | $-\text{N}(\text{CH}_3)_2$ | O | CH | m.p. 100~102° C. |
| 14 | " | " | S | " | n$_D^{21.8}$ 1.5030 |
| 15 | " | " | " | N | Oily product |

TABLE 1-continued

| | | | | | |
|---|---|---|---|---|---|
| 16 | " | 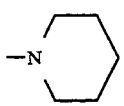 (piperidinyl) | O | CH | $n_D^{22.4}$ 1.5049 |
| 17 | CH$_2$=CHCH$_2$— | —N(CH$_3$)$_2$ | " | " | $n_D^{22.5}$ 1.5110 |
| 18 | " | 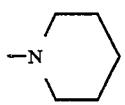 (piperidinyl) | " | " | m.p. 115~118° C. |
| 19 | " | —N(CH$_3$)$_2$ | S | " | |
| 20 | CH$_2$=CHCH$_2$— | 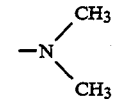 (piperidinyl) | S | CH | |
| 21 | CH≡CCH$_2$— | —N(CH$_3$)$_2$ | " | " | $n_D^{24.6}$ 1.5044 |
| 22 | " | 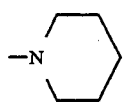 (piperidinyl) | O | " | m.p. 160~164° C. |
| 23 | FCH$_2$CH$_2$— | —N(CH$_3$)$_2$ | " | " | m.p. 94~96° C. |
| 24 | " | 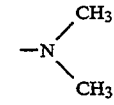 (piperidinyl) | " | " | m.p. 92~95° C. |
| 25 | ClCH$_2$CH$_2$— | " | " | " | $n_D^{22.6}$ 1.5028 |
| 26 | NCCH$_2$CH$_2$— | —N(CH$_3$)$_2$ | " | " | $n_D^{24.6}$ 1.5072 |
| 27 | " | 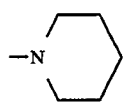 (piperidinyl) | " | " | m.p. 135~137° C. |
| 28 | CH$_3$ | —NHCH$_3$ | S | CH | m.p. 127~128° C. |
| 29 | " | " | " | N | m.p. 132~134° C. |
| 30 | " | —NHC$_2$H$_5$ | " | CH | m.p. 163~165° C. |
| 31 | " | " | " | N | $n_D^{23.7}$ 1.5206 |
| 32 | CH$_3$ | —NHC$_3$H$_7$-n | S | CH | m.p. 119~120° C. |
| 33 | " | " | " | N | $n_D^{23.1}$ 1.5067 |
| 34 | " | —NHC$_3$H$_7$-i | " | CH | m.p. 146~148° C. |
| 35 | " | " | " | N | m.p. 124~126° C. |
| 36 | " | " | O | CH | m.p. 161~163° C. |
| 37 | " | —NHCH$_2$CH=CH$_2$ | S | " | m.p. 119~120° C. |
| 38 | " | " | " | N | $n_D^{24.3}$ 1.5363 |
| 39 | " | —NHCH$_2$C≡CH | " | CH | $n_D^{22.2}$ 1.5330 |
| 40 | " | " | " | N | m.p. 132~133° C. |
| 41 | " | " | O | CH | m.p. 101~103° C. |

TABLE 1-continued

| Compound | R⁴ | (NR²R³ group) | X | Z | Physical property |
|---|---|---|---|---|---|
| 42 | " | —NH—C₆H₅ (phenyl) | S | " | m.p. 147~148° C. |
| 43 | " | " | " | N | m.p. 177~178° C. |
| 44 | CH₃ | —NHCH₂—C₆H₅ | S | CH | m.p. 150~151° C. |
| 45 | " | " | " | N | $n_D^{21.4}$ 1.5598 |
| 46 | " | —N(OCH₃)(CH₃) | " | CH | Oily product |
| 47 | " | " | " | N | Oily product |
| 48 | " | —N(morpholino) | " | CH | Oily product |
| 49 | " | " | " | N | m.p. 74~77° C. |
| 50 | C₂H₅ | —NHCH₃ | " | CH | $n_D^{24.6}$ 1.5366 |
| 51 | " | " | " | N | $n_D^{24.3}$ 1.5216 |
| 52 | " | —N(OCH₃)(CH₃) | " | " | $n_D^{25.3}$ 1.5152 |
| 53 | C₃H₇-n | —NHCH₃ | " | CH | $n_D^{23.4}$ 1.5210 |
| 54 | " | " | " | N | |
| 55 | C₃H₇-n | —N(OCH₃)(CH₃) | S | CH | $n_D^{24.4}$ 1.5174 |
| 56 | " | " | " | N | $n_D^{24.4}$ 1.5098 |
| 57 | CH≡CCH₂— | " | O | CH | $n_D^{24.8}$ 1.5111 |
| 58 | CH₃ | —NHC₄H₉-n | S | " | m.p. 91~94° C. |
| 59 | " | " | " | N | m.p. 115~118° C. |
| 60 | " | —NHC₅H₁₁-n | " | CH | m.p. 96~98° C. |
| 61 | " | " | " | N | $n_D^{27.4}$ 1.5108 |
| 62 | " | —NHC₆H₁₃-n | " | CH | m.p. 94~96° C. |
| 63 | " | " | " | N | |
| 64 | " | —NHC₄H₉-t | " | CH | m.p. 129~132° C. |
| 65 | " | " | " | N | m.p. 112~114° C. |

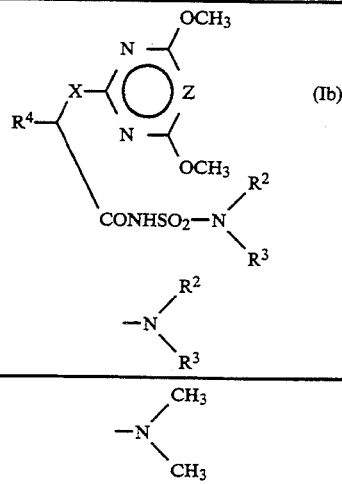

(Ib)

| Compound | R⁴ | —NR²R³ | X | Z | Physical property |
|---|---|---|---|---|---|
| 66 | C₃H₇-n | —N(CH₃)(CH₃) | S | CH | m.p. 90~92° C. |

TABLE 1-continued

| Compound | R¹ | R⁵ (structure) | | | Physical property |
|---|---|---|---|---|---|
| 67 | " | piperidine (-N<ring>) | " | " | $n_D^{23.2}$ 1.5380 |
| 68 | $C_3H_7$-i | -N(CH₃)₂ | " | " | m.p. 110~111° C. |
| 69 | " | piperidine (-N<ring>) | " | " | m.p. 74~76° C. |
| 70 | $C_4H_9$-t | -N(CH₃)₂ | O | " | |
| 71 | " | " | S | " | m.p. 106~108° C. |
| 72 | " | " | " | N | |
| 73 | " | piperidine (-N<ring>) | " | CH | m.p. 112~115° C. |

$$R^1-O\underset{\underset{CH_2}{\underset{|}{CONHSO_2-R^5}}}{\overset{\overset{CH_3}{|}}{\underset{|}{C}}}-\overset{H}{\underset{|}{C}}-X-\underset{N}{\overset{N}{\underset{}{\bigcirc}}}\begin{matrix}OCH_3\\Z\\OCH_3\end{matrix} \quad (Ic)$$

| Compound | R¹ | R⁵ | X | Z | Physical property |
|---|---|---|---|---|---|
| 74 | CH₃ | 2-pyridyl | O | CH | m.p. 128~130° C. |
| 75 | " | " | S | " | m.p. 158~160° C. |
| 76 | " | " | " | N | m.p. 152~155° C. |
| 77 | " | 4-pyridyl | " | CH | m.p. 147~149° C. |
| 78 | " | 3-pyridyl | " | " | m.p. 139~141° C. |
| 79 | " | 3-methyl-2-pyridyl | " | " | cannot be meassured |
| 80 | " | 6-methyl-2-pyridyl | " | " | " |

TABLE 1-continued
| 81 | CH₃ | 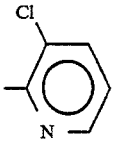 | S | CH | |
| 82 | " | 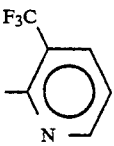 | " | " | m.p. 83~86° C. |
| 83 | " | " | " | N | $n_D^{22.0}$ 1.5250 |
| 84 | " | 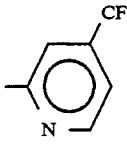 | " | CH | |
| 85 | " | " | " | N | |
| 86 | " | 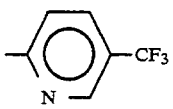 | " | CH | m.p. 135~139° C. |
| 87 | " | " | " | N | $n_D^{22.7}$ 1.5226 |
| 88 | C₂H₅ | 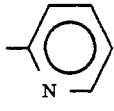 | " | " | m.p. 176~179° C. |
| 89 | " | " | O | " | m.p. 155~158° C. |
| 90 | C₂H₅ | 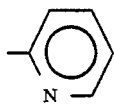 | S | CH | $n_D^{24.9}$ 1.5290 |
| 91 | " | 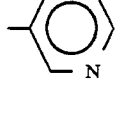 | " | " | m.p. 45~49° C. |
| 92 | " |  | " | " | m.p. 50~54° C. |
| 93 | C₃H₇-n | 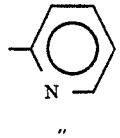 | " | " | m.p. 146~149° C. |
| 94 | " | " | " | N | m.p. 116~120° C. |
| 95 | " | 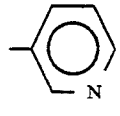 | " | CH | m.p. 105~107° C. |
| 96 | " | 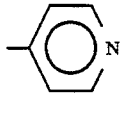 | " | " | m.p. 138~141° C. |

TABLE 1-continued
| 97 | CH$_2$=CHCH$_2$— | 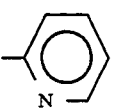 | O | " | m.p. 108~111° C. |
| --- | --- | --- | --- | --- | --- |
| 98 | CH≡CCH$_2$— | " | " | " | m.p. 72~75° C. |
| 99 | " | " | S | " | m.p. 146~149° C. |
| 100 | FCH$_2$CH$_2$— | " | O | " | m.p. 112~114° C. |
| 101 | ClCH$_2$CH$_2$— | 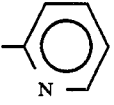 | O | CH | 143° C. decomposed |
| 102 | " | " | S | " | |
| 103 | NCCH$_2$CH$_2$— | " | O | " | 150° C. decomposed |
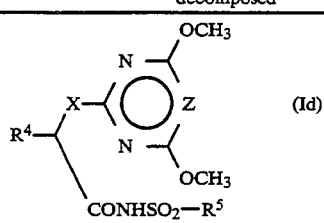
(Id)
| Compound | R$^4$ | R$^5$ | X | Z | Physical property |
| --- | --- | --- | --- | --- | --- |
| 104 | C$_3$H$_7$-n | 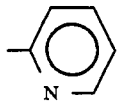 | S | CH | m.p. 166~167° C. |
| 105 | " | " | " | N | |
| 106 | " | 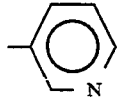 | " | CH | m.p. 116~118° C. |
| 107 | C$_3$H$_7$-n | 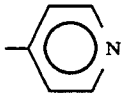 | S | CH | m.p. 122~124° C. |
| 108 | C$_3$H$_7$-i | 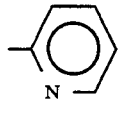 | " | " | m.p. 167~169° C. |
| 109 | " | " | " | N | |
| 110 | " | 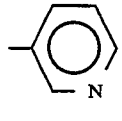 | " | CH | m.p. 135~136° C. |
| 111 | " | 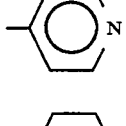 | " | " | m.p. 161~163° C. |
| 112 | C$_4$H$_9$-t | 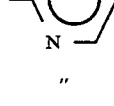 | O | " | |
| 113 | " | " | S | " | m.p. 166~168° C. |
| 114 | " | " | " | N | |

TABLE 1-continued

| | | | |
|---|---|---|---|
| 115 | " | 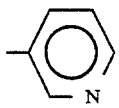 | CH |
| 116 | " | 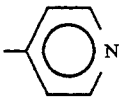 | " " |

In the above exemplary compounds, particularly preferred compounds are Compounds Nos. 1, 2, 30, 32, 39, 46, 68, 71, 74, 75, 108 and 113.

Example 2

(1) Preparation of Granule 8 parts by weight of Compound 1 was uniformly mixed with 30 parts by weight of bentonite, 59 parts by weight of talc, 1 part by weight of Neopelex powder (trade name, produced by Kao K.K., Japan) and 2 parts by weight of sodium lignosulfonate, and then the mixture was kneaded with addition of a small amount of water, followed by granulation and drying, to obtain a granule.

(2) Preparation of Wettable Powder 50 parts by weight of Compound 2 was uniformly mixed with 46 parts by weight of kaolin, 2 parts by weight of Neopelex powder (trade name, produced by Kao K.K., Japan) and 2 parts by weight of Demol N (trade name, produced by Kao K.K., Japan), and then the mixture was pulverized to obtain a wettable powder.

(3) Preparation of Emulsion 30 parts by weight of Compound 3 was added to 60 parts by weight of xylene, 5 parts by weight of dimethylformamide and 5 parts by weight of Sorpol 3005X (trade name, produced by Toho Kagaku Kogyo, Japan) and uniformly mixed to be dissolved therein to obtain an emulsion.

(4) Preparation of Dust 5 parts by weight of Compound 4 was uniformly mixed with 50 parts by weight of talc and 45 parts by weight of clay to obtain a dust.

Example 3

(1) Herbicidal test for paddy field

Wagner pots, each having an area of 1/5000 are, were packed with Ube soil (alluvial soil) and planted with seeds or tubers of weeds (barnyardgrass, bulrush and flatstage). Then, the pots were filled with water to a depth of 3 cm.

Each wettable powder of the desired compounds (I) shown in Table 1 prepared in accordance with Example 2 was diluted with water and subjected to dropwise addition treatment by using pipet so that an effective concentration of the compound (I) in each herbicide became 20 g/are at 1 leaf stage of barnyardgrass. These plants were controlled in a glass house at an average temperature of 25° C. for 3 weeks, and then herbicidal effects thereof were investigated.

The herbicidal effects were evaluated according to the 6 ranks (0: None (normal development), 1: Less damaged, 2: Slightly damaged, 3: Moderately damaged, 4: Severely damaged and 5: All killed) as compared with non-treated district.

The results are shown in Table 2.

TABLE 2

| | Kind of weed | | | | Kind of weed | | |
|---|---|---|---|---|---|---|---|
| Compound | Barnyardgrass | Bulrush | Flatstage | Compound | Barnyardgrass | Bulrush | Flatstage |
| 1 | 5 | 5 | 5 | 46 | 5 | 5 | 5 |
| 2 | 5 | 5 | 5 | 48 | 5 | 5 | 5 |
| 3 | 5 | 5 | 4 | 50 | 5 | 5 | 5 |
| 5 | 4 | 5 | 4 | 52 | 3 | 5 | 4 |
| 7 | 5 | 5 | 5 | 53 | 5 | 4 | 4 |
| 10 | 4 | 5 | 4 | 55 | 5 | 5 | 5 |
| 14 | 5 | 5 | 5 | 58 | 5 | 4 | 5 |
| 15 | 4 | 5 | 4 | 66 | 5 | 5 | 4 |
| 28 | 5 | 5 | 5 | 67 | 5 | 5 | 4 |
| 29 | 5 | 5 | 5 | 68 | 5 | 5 | 5 |
| 34 | 5 | 5 | 5 | 69 | 5 | 5 | 5 |
| 35 | 5 | 5 | 4 | 71 | 5 | 5 | 5 |
| 36 | — | 5 | 4 | 73 | 5 | 5 | 4 |
| 37 | 5 | 5 | 5 | 75 | 4 | 5 | 3 |
| 39 | 5 | 5 | 5 | 76 | 5 | 5 | 5 |
| 40 | 3 | 5 | 4 | 79 | 5 | 5 | 4 |
| 41 | 5 | 5 | 5 | 90 | 5 | 5 | 2 |
| 42 | 5 | 5 | 3 | 91 | 5 | 5 | 3 |
| 44 | 5 | 5 | 5 | 93 | 4 | 5 | 3 |
| 45 | 5 | 5 | 4 | 96 | 5 | 5 | 5 |

(2) Soil treatment test for upland field

Wagner pots, each having an area of 1/5000 are, were packed with Ube soil (alluvial soil), and then each seed of cotton, soy bean, crabgrass, barnyardgrass, velvetleaf, common lambsquarter, livid amaranthus, morning glory and cocklebur were planted and covered with soil.

Each wettable powder of the desired compounds (I) shown in Table 1 prepared in accordance with Example 2 was diluted with water and uniformly sprayed on the surface of each soil so that an effective concentration of the compound (I) in each herbicide became 20 g/are. These plants were controlled in a glass house at an average temperature of 25° C. for 3 weeks, and then herbicidal effects thereof were investigated.

The herbicidal effects were evaluated according to the evaluation method described in (1) herbicidal test for paddy field, and the results are shown in Table 3 with the results of Comparative chemical used in (1).

TABLE 3

| Compound | Crop | | Kind of weed | | | | | | |
|---|---|---|---|---|---|---|---|---|---|
| | Cotton | Soy bean | Crab-grass | Barnyard-grass | Velvet leaf | Common lambsquarter | Livid amaranthus | Morning glory | Cockle-bur |
| 1 | 0 | 2 | 4 | 5 | 5 | 5 | 5 | 4 | 4 |
| 2 | 1 | 1 | 5 | 5 | 5 | 5 | 5 | 5 | 4 |
| 3 | 1 | 1 | 5 | 5 | 5 | 4 | 5 | 5 | 5 |
| 5 | 0 | 1 | 5 | 5 | 5 | 4 | 5 | 5 | 5 |
| 7 | 0 | 1 | 4 | 3 | 4 | 5 | 4 | 4 | 4 |
| 14 | 0 | 0 | 4 | 4 | 3 | 4 | 5 | 4 | 4 |
| 15 | 0 | 0 | 4 | 4 | 4 | 4 | 5 | 4 | 4 |
| 28 | 0 | — | 5 | 3 | 5 | 5 | 3 | 5 | 3 |
| 29 | — | — | 5 | 5 | 5 | 5 | 5 | 5 | 5 |
| 32 | — | — | 5 | 4 | 3 | 3 | 5 | 4 | — |
| 34 | 2 | — | 5 | 4 | 5 | 4 | — | 5 | — |
| 35 | 0 | 0 | 3 | 3 | 4 | 3 | — | 5 | — |
| 37 | 2 | 2 | 5 | 5 | 5 | 5 | 4 | 4 | 5 |
| 38 | 1 | 2 | 5 | 3 | 3 | 3 | 3 | 4 | 4 |
| 39 | 0 | 2 | 5 | 3 | 5 | 5 | 5 | 4 | 5 |
| 40 | 0 | — | 5 | 5 | 4 | — | 5 | 4 | — |
| 42 | 2 | — | 5 | 5 | 4 | — | — | 4 | — |
| 48 | — | — | 5 | 4 | 5 | 5 | 5 | 5 | 4 |
| 50 | 0 | — | 4 | 5 | 5 | 4 | 5 | 5 | 3 |
| 52 | 0 | 1 | 3 | 4 | 5 | 4 | 4 | 5 | 3 |
| 53 | — | — | 5 | 4 | 4 | 4 | 4 | 4 | 3 |
| 55 | 1 | — | 4 | — | 3 | 4 | 4 | 4 | — |
| 56 | 0 | — | 5 | 5 | 5 | 4 | 4 | 3 | 5 |
| 58 | 0 | — | 5 | 5 | 5 | 3 | 5 | 3 | 5 |
| 66 | 0 | — | 4 | 5 | 3 | 3 | 3 | — | — |
| 68 | 0 | — | 4 | 4 | 3 | 3 | 3 | — | — |
| 69 | 0 | — | 5 | 4 | 3 | 4 | 4 | 4 | 3 |
| 71 | 0 | — | 5 | 5 | 5 | 5 | 5 | — | — |
| 73 | 0 | — | 5 | 5 | 5 | 5 | 5 | — | 4 |
| 75 | 0 | — | 4 | 4 | 4 | 3 | 4 | 5 | 5 |
| 76 | 0 | — | 5 | 4 | 5 | 4 | 4 | 5 | 5 |
| 77 | 0 | 0 | 3 | 4 | 5 | 4 | 3 | 5 | 4 |
| 78 | 0 | 0 | 3 | 2 | 3 | 2 | 2 | 4 | 5 |
| 79 | 0 | — | 3 | 3 | 5 | 2 | 3 | 5 | 5 |
| 83 | 0 | — | 4 | 4 | 5 | 3 | 4 | 5 | 4 |
| 89 | 0 | 0 | 2 | 3 | 3 | 1 | 2 | 5 | 4 |
| 93 | 0 | — | 3 | 2 | 4 | 2 | 3 | 5 | 5 |
| 96 | 1 | 3 | 1 | 2 | 5 | 3 | 3 | 5 | 5 |

(3) Foliar spread test for upland field

Wagner pots, each having an area of 1/5000 are, were packed with volcanic ash soil and then each seed of cotton, soy bean, crabgrass, barnyardgrass, velvetleaf, common lambsquarter, livid amaranthus, morning glory and cocklebur was planted, covered with soil and grown for 2 weeks.

Each wettable powder of the desired compounds (I) shown in Table 1 prepared in accordance with Example 2 was diluted to 2000 ppm with water containing a spreading agent Neoesterin (trade name, produced by Kumiai Kagaku Co., Japan) (500 ppm) and then uniformly sprayed on the above respective plants. After these plants were controlled in a glass house at an average temperature of 25° C. for 3 weeks, the herbicidal effects thereof were investigated.

The herbicidal effects were evaluated according to the evaluation method described in (1) herbicidal test for paddy field, and the results are shown in Table 4 with the results of Comparative chemical used in (1).

TABLE 4

| Compound | Kind of weed | | | | | | |
|---|---|---|---|---|---|---|---|
| | Grab-grass | Barnyard-grass | Velvet leaf | Common lambsquarter | Livid amaranthus | Morning glory | Cocklebur |
| 1 | 4 | — | 4 | — | — | 5 | 5 |
| 2 | 5 | 5 | 5 | 5 | 4 | 5 | 5 |
| 3 | 5 | — | 5 | — | — | 5 | 5 |
| 5 | — | — | 4 | — | — | 5 | 4 |
| 7 | — | — | 4 | 4 | 3 | 5 | 5 |
| 14 | — | — | 4 | — | — | 5 | 5 |
| 15 | — | — | 4 | — | — | 5 | 5 |
| 28 | 5 | 5 | 5 | 5 | 5 | 5 | 5 |
| 29 | 5 | 5 | 5 | 5 | — | 5 | 5 |
| 32 | 4 | 5 | 5 | 5 | — | 5 | 5 |
| 34 | 3 | 5 | 5 | 5 | — | 5 | 5 |
| 35 | 5 | 5 | 5 | 5 | — | 5 | 5 |
| 36 | — | — | 5 | — | 4 | 5 | 5 |
| 37 | 5 | 5 | 5 | 5 | 5 | 1 | 5 |
| 38 | — | — | 5 | 5 | 5 | 5 | 5 |
| 39 | 5 | 5 | 5 | 5 | — | 5 | 5 |
| 40 | — | 3 | 5 | — | — | 5 | 5 |
| 41 | 5 | 5 | 5 | — | — | 5 | 5 |
| 42 | 5 | 5 | 5 | — | 5 | 5 | 5 |
| 44 | — | 3 | 5 | 5 | 5 | 5 | 5 |

TABLE 4-continued

| | | | | | | | | |
|---|---|---|---|---|---|---|---|---|
| 46 | — | 5 | 5 | — | 5 | 5 | 5 | |
| 47 | — | — | 5 | — | 5 | 5 | 5 | |
| 48 | — | 3 | 5 | 5 | 5 | 5 | 5 | |
| 49 | — | 5 | 5 | — | 5 | 5 | 5 | |
| 50 | 3 | — | 5 | — | — | 5 | 5 | |
| 51 | 5 | 5 | 5 | 5 | 5 | 5 | 5 | |
| 53 | — | 5 | 5 | — | — | 5 | 5 | |
| 55 | 5 | — | 5 | — | — | 5 | 5 | |
| 56 | — | 3 | 5 | — | — | 5 | 5 | |
| 58 | — | — | 5 | — | — | 5 | 5 | |
| 59 | — | — | 5 | — | — | 4 | 4 | |

| | Crop | | Kind of weed | | | | | |
|---|---|---|---|---|---|---|---|---|
| Compound | Cotton | Soy bean | Crab-grass | Barn-yard-grass | Velvet leaf | Common lambs-quarter | Livid amaranthus | Morning glory | Cockle-bur |
| 66 | 1 | — | — | — | 4 | 5 | 5 | 5 | 5 |
| 68 | 0 | — | — | — | 5 | 5 | 4 | 5 | 4 |
| 69 | 0 | — | — | — | 4 | 4 | 4 | 5 | 4 |
| 71 | 2 | — | — | — | 5 | 5 | 5 | 5 | 5 |
| 73 | 1 | — | 3 | 5 | 4 | 5 | 5 | 5 | 5 |
| 75 | 0 | — | 5 | 5 | 4 | 5 | 5 | 4 | 5 |
| 76 | 1 | — | 4 | 5 | 5 | 4 | 4 | 3 | 4 |
| 78 | 0 | 2 | 4 | 5 | 4 | 4 | 3 | 4 | 4 |
| 93 | 0 | 1 | 4 | 3 | 3 | 4 | 5 | 4 | 5 |
| 96 | 2 | — | 5 | 5 | 4 | 4 | 4 | 4 | 5 |
| 108 | 1 | — | 3 | 5 | 5 | 5 | 5 | 5 | 4 |
| 113 | — | — | 3 | 4 | 5 | 5 | 5 | 5 | 5 |

The novel sulfonamide derivative of the present invention shows excellent herbicidal effect, particularly effective on annual grass weeds and broad-leaved weeds, and also has high selectivity to crops such as cotton and soy bean.

We claim:

1. A sulfonamide compound represented by the following formula (I):

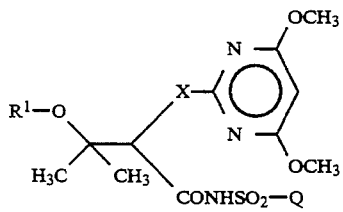

(I)

wherein $R^1$ represents a lower alkyl group, a lower alkenyl group, a lower alkynyl group, a halo-lower alkyl group or a cyano-lower alkyl group; Q represents an unsubstituted pyridyl group, a pyridyl group substituted by at least one of an alkyl group having 1 to 6 carbon atoms, a halogen atom, a haloalkyl group having 1 to 6 carbon atoms and an alkoxy group having 1 to 6 carbon atoms, or —$NR^2R^3$ where $R^2$ represents a hydrogen atom, an alkyl group having 1 to 6 carbon atoms, an alkoxy group having 1 to 6 carbon atoms; and $R^3$ represents an alkyl group having 1 to 6 carbon atoms, an alkenyl group having 2 to 6 carbon atoms, an alkynyl group having 2 to 6 carbon atoms, a phenyl group or a benzyl group; or $R^2$ and $R^3$ may be combined to form a 3- to 8-membered cycloamino group, a piperidinyl group or a morpholino group; and X represents an oxygen atom or a sulfur atom.

2. The compound according to claim 1, wherein said compound is a 3-alkoxy-N-(N-substituted amino)sulfonylalkanoic acid amide compound represented by the following formula (Ia):

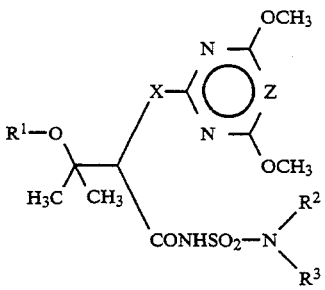

(Ia)

wherein $R^1$, $R^2$, $R^3$, and X each have the same meanings as defined in claim 1, and Z is a —CH= group.

3. The compound according to claim 1, wherein said compound is a 3-alkoxy-N-pyridylsulfonylalkanoic acid amide derivative represented by the following formula (Ic):

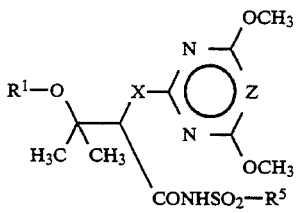

(Ic)

wherein $R^1$ and X each have the same meanings as defined in claim 1; Z is a —CH= group; and $R^5$ represents an unsubstituted pyridyl group, a pyridyl group substituted by at least one of an alkyl group having 1 to 6 carbon atoms, a halogen atom, a haloalkyl group having 1 to 6 carbon atoms and an alkoxy group having 1 to 6 atoms.

4. The compound according to claim 1, wherein $R^1$ is a $C_{1-4}$ alkyl group, a $C_{2-6}$ alkenyl group, a $C_{2-6}$ alkynyl group, a halo-$C_{1-6}$ alkyl group or a cyano-$C_{1-6}$ alkyl group.

5. The compound according to claim 4, wherein $R^1$ is a methyl group, an ethyl group, an n-propyl group, an isopropyl group, an allyl group, a propargyl group, a fluoroethyl group, a chloroethyl group or a cyanoethyl group.

6. The compound according to claim 1, wherein Q is 2-pyridyl group, 3-pyridyl group, 4-pyridyl group or —$NR^2R^3$ where $R^2$ is a hydrogen atom, a $C_{1-6}$ alkyl group or a $C_{1-6}$ alkoxy group; and $R^3$ is a $C_{1-6}$ alkyl group, a $C_{2-6}$ alkenyl group, a $C_{2-6}$ alkynyl group, a phenyl group or a benzyl group; or $R^2$ and $R^3$ may be combined to form a piperidinyl group or a morpholino group.

7. The compound according to claim 6, wherein Q is 2-pyridyl group, 3-pyridyl group, 4-pyridyl group or —$NR^2R^3$ where $R^2$ is a hydrogen atom, a methyl group or a methoxy group; and $R^3$ is a methyl group, an ethyl group, an n-propyl group, an isopropyl group, an n-butyl group, a t-butyl group, an n-pentyl group, an n-hexyl group, an allyl group, a propargyl group, a phenyl group or a benzyl group; or $R^2$ and $R^3$ may be combined to form a piperidinyl group or a morpholino group.

8. The compound according to claim 1, wherein the compound is at least one selected from the group consisting of 2-(4,6-dimethoxypyrimidin-2-yl)thio-N-(N,N-dimethylamino)sulfonyl- 3-methoxy-3-methylbutanoic acid amide, 2-(4,6-dimethoxypyrimidin-2-yl)oxy-N-(N,N-dimethylamino)sulfonyl-3-methoxy-3-methyl-butanoic acid amide, 2-(4,6-dimethoxypyrimidin-2-yl)thio-N-(N-ethylamino)sulfonyl-3-methoxy-3-methyl-butanoic acid amide, 2-(4,6-dimethoxypyrimidin-2-yl)thio-N-(N-n-propylamino)sulfonyl-3-methoxy-3-methylbutanoic acid amide, 2-(4,6-dimethoxypyrimidin-2-yl)thio-N-(N-propargylamino)sulfonyl-3-methoxy-3-methylbutanoic acid amide, 2-(4,6-dimethoxypyrimidin-2 -yl)thio-N-(N-methoxy-N-methylamino)sulfonyl-3-methoxy-3-methylbutanoic acid amide, 2-(4,6-dimethoxypyrimidin-2-yl)thio-3-methoxy-3-methyl-N-(pyridin-2-yl)sulfonylbutanoic acid amide, 2-(4,6-dimethoxypyrimidin-2-yl)oxy-3-methoxy-3-methyl-N-(pyridin-2-yl)sulfonylbutanoic acid amide.

9. A herbicidal composition comprising the sulfonamide compound (I) according to claim 1 as an active ingredient and a herbicidally effective carrier.

* * * * *